(12) United States Patent
Piraka

(10) Patent No.: US 6,520,977 B2
(45) Date of Patent: Feb. 18, 2003

(54) UTERINE BALLOON APPARATUS AND METHOD

(76) Inventor: Hadi Piraka, 21257 Woodfarm Dr., Northville, MI (US) 48167

( * ) Notice: Subject to any disclaimer, the term of this patent is extended or adjusted under 35 U.S.C. 154(b) by 39 days.

(21) Appl. No.: 09/780,708

(22) Filed: Feb. 12, 2001

(65) Prior Publication Data

US 2001/0007945 A1 Jul. 12, 2001

Related U.S. Application Data

(63) Continuation-in-part of application No. 09/455,254, filed on Dec. 6, 1999, now abandoned.

(51) Int. Cl.$^7$ .............................................. A61M 29/00
(52) U.S. Cl. ....................................... 606/193; 607/104
(58) Field of Search ............................. 606/104, 27–31, 606/114, 193, 33; 607/104, 105, 113, 101

(56) References Cited

U.S. PATENT DOCUMENTS 5,571,153 A * 11/1996 Wallsten ..................... 604/114
5,957,962 A * 9/1999 Wallsten et al. .............. 606/27

* cited by examiner

Primary Examiner—Kevin T. Truong
(74) Attorney, Agent, or Firm—Alex Rhodes

(57) ABSTRACT

A uterine balloon apparatus and method for countering hemorrhaging in a patient after childbirth. The balloon apparatus is comprised of a balloon, a physiologic fluid, such as a normal saline solution and a control. A characteristic feature of the invention is that a fluid pressure inside of the balloon is maintained at a safe level by the control as a uterus contracts to resume its physiologic function. The control is comprised of a pressure relief valve, a pressure regulator valve, a fill valve and flexible tubing. Another characteristic feature of the invention is that the fluid pressure inside of the balloon is prevented from exceeding a level which would cause a premature ejection of the balloon or damage to the uterus. The balloon in an inflated state, is inserted into the uterus with the assistance of a catheter which extends part way into the interior of the balloon. After the balloon has been inserted, a sufficient quantity of a warm physiologic fluid, such as a normal saline solution is infused into the balloon to distend the balloon against the uterine wall and terminate bleeding. When bleeding has been terminated, the pressure regulator valve is adjusted to prevent the pressure in the balloon from rising during contractions of the uterus. When the pressure begins to rise, the pressure regulator valve opens and some of the physiologic fluid is released to maintain the pressure at a safe level. An optional pressure gauge and high/low pressure warning systems are provided to monitor the operation of the balloon apparatus.

26 Claims, 5 Drawing Sheets

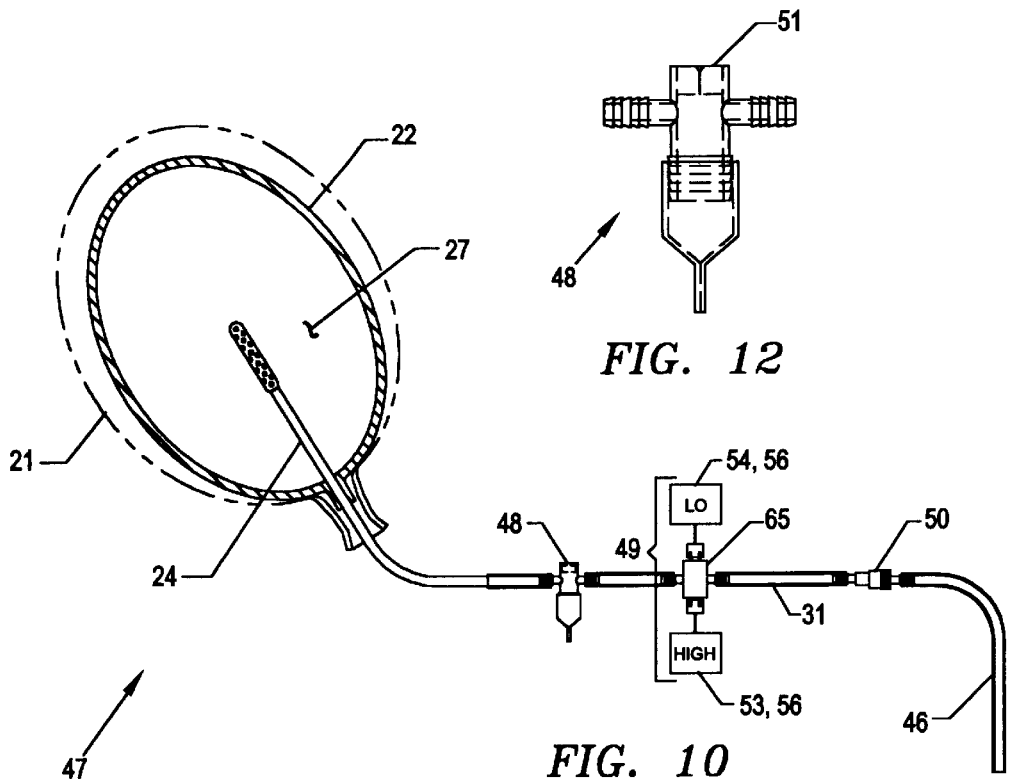
FIG. 12
FIG. 10
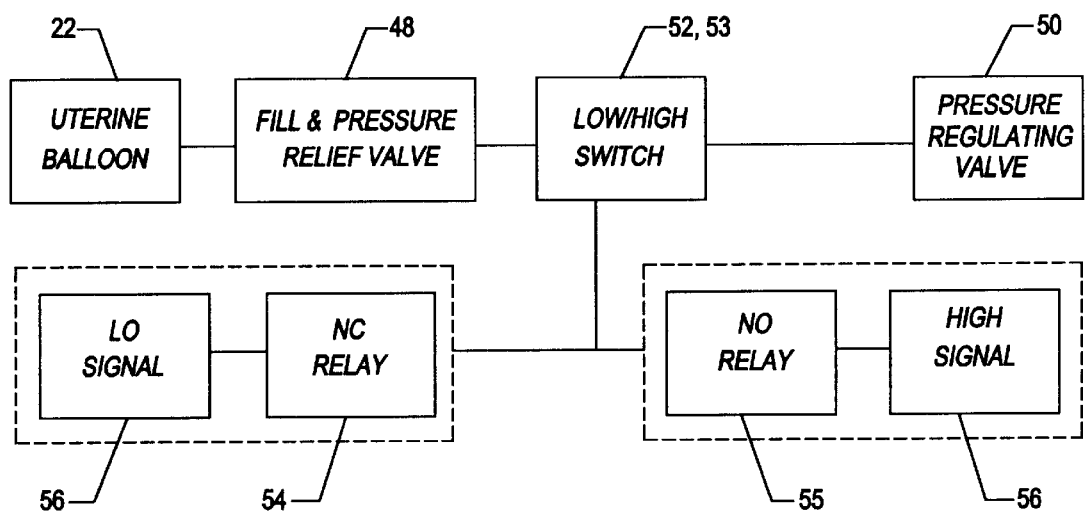
FIG. 11

UTERINE BALLOON APPARATUS AND METHOD

This is a Continuation-in-part of application Ser. No. 09/455,254, filed on Dec. 6, 1999, now abandoned.

FIELD OF THE INVENTION

This invention relates to the surgical art of controlling bleeding and more specifically to an uterine balloon apparatus and method for countering maternal hemorrhaging.

BACKGROUND OF THE INVENTION

Maternal hemorrhage following childbirth is a major life-threatening condition. Various remedies are in use to stop hemorrhaging, including packing the uterus and blocking the uterine arteries. However, these remedies may not work or may be associated with high blood loss. A hemorrhaging patient after childbirth may be subject to major procedures, such as mass blood transfusions, hysterectomy, or in some instances may result in a loss of her life.

SUMMARY OF THE INVENTION

The present invention is a major advancement for treating post childbirth hemorrhaging. Its primary object is to provide an alternative to surgical procedures and blood transfusions for countering excessive uterine bleeding. Major surgical procedures and blood transfusions have inherent risks which can be life threatening. The invention is particularly useful when bleeding occurs at multiple sites in a uterine wall. When such bleeding occurs surgery and/or blood transfusion are often used to manage an excessive loss of blood.

The invention comprises a balloon which is filled with a with a physiologic solution, such as a sterile saline solution which is inserted into a uterus and a control for maintaining a constant pressure inside the balloon as the uterus contracts after childbirth to resume its normal physiologic function. The inflated balloon presses against the uterine wall to check the flow of bleeding from the wall. One benefit of the balloon is that it is effective when bleeding occurs at multiple sites in the uterine wall.

The control may take on various forms, each of which produces a gradual discharge of fluid from the balloon to maintain a constant pressure inside of the balloon as the uterus contracts after childbirth to resume its rhythmic contractions. The control includes a series of valves which are believed to be novel. In one aspect of the invention, the control includes a combination fill and pressure regulating valve. In another aspect of the invention the control includes a combination fill and pressure relief valve. In still another aspect of the invention the control includes a high/low pressure warning device.

In employing the teaching of the present invention, a plurality of alternate constructions can be adopted to achieve the desired results and capabilities. In this disclosure, only several aspects of the invention are discussed. However, these aspects are intended as examples and should not be considered as limiting the scope of the invention.

Further features and benefits will be apparent by reference to the drawings and ensuing detailed description of a preferred embodiment which discloses the best mode contemplated in carrying out the invention. The exclusive rights which are claimed are set forth in the numbered claims following the detailed description of the preferred embodiment.

BRIEF DESCRIPTION OF THE DRAWINGS

The invention will be better understood and further objects, characterizing features, details and advantages thereof will appear more clearly with reference to the diagrammatic drawings illustrating specific embodiments of the invention by way of non-limiting example only.

FIG. 10 is a view of an alternate embodiment of the invention.

FIG. 11 is block diagram of the alternate embodiment.

FIG. 12 is an enlarged front view of a combination fill and pressure relief valve.

DETAILED DESCRIPTION OF A PREFERRED EMBODIMENT

Figure 1:
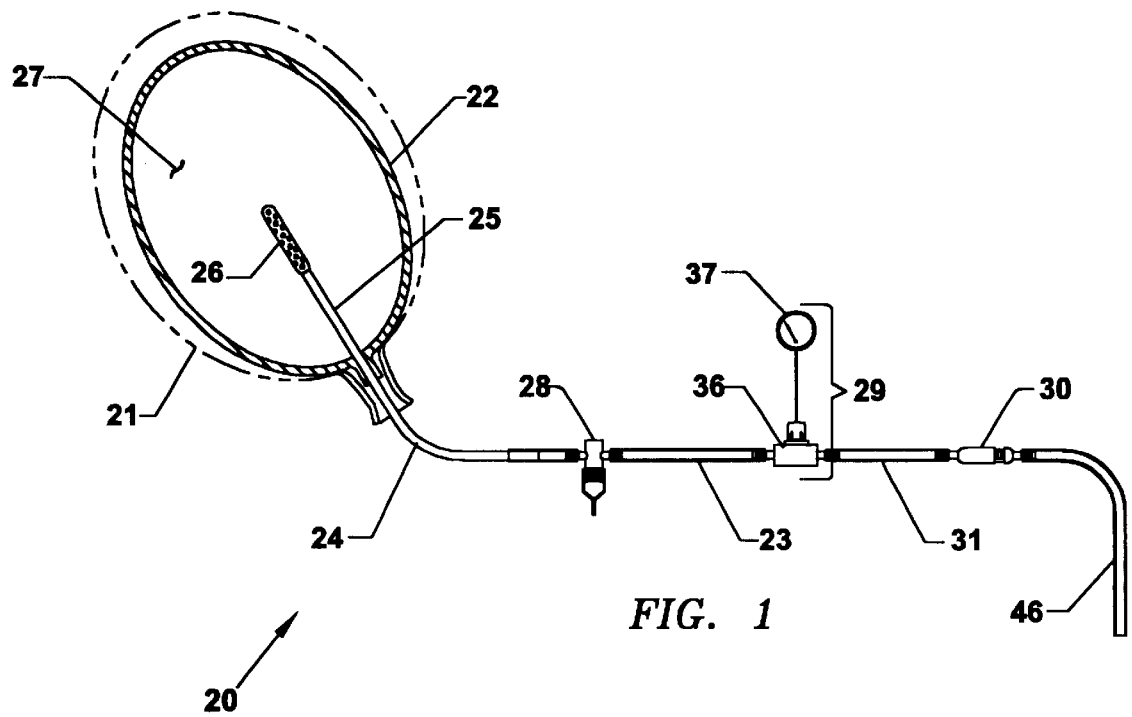
FIG. 1 is a view of a balloon and control for countering uterine bleeding according to the present invention.
Figure 2:
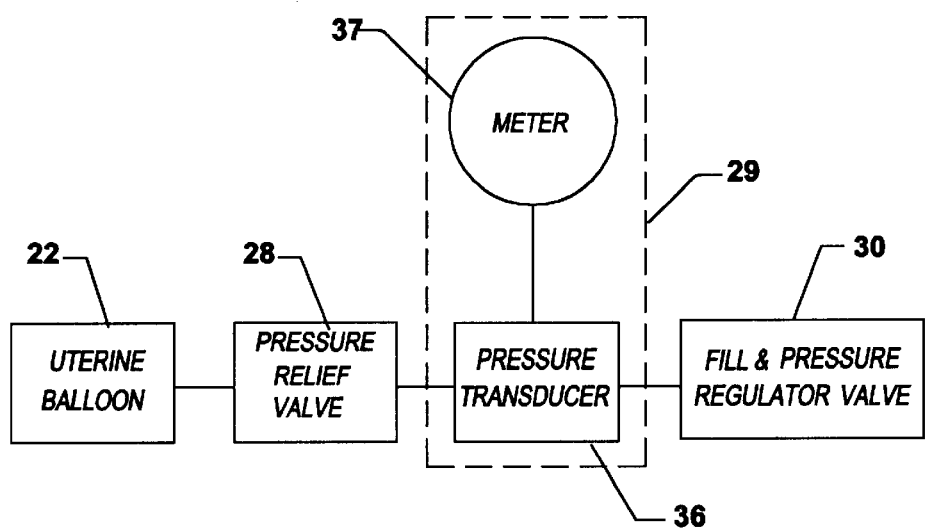
FIG. 2 is a block diagram of the balloon and control.
Figure 6:
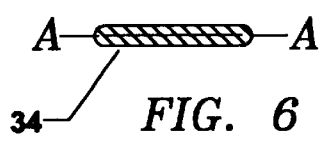
FIG. 6 is a cross-sectional view taken on the line 6—6 in FIG. 5.
Figure 3:
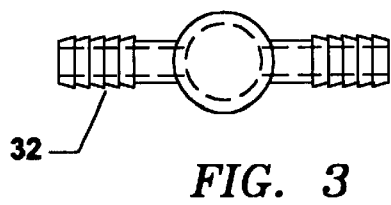
FIG. 3 is an enlarged plan view of a pressure relief valve.
Figure 5:
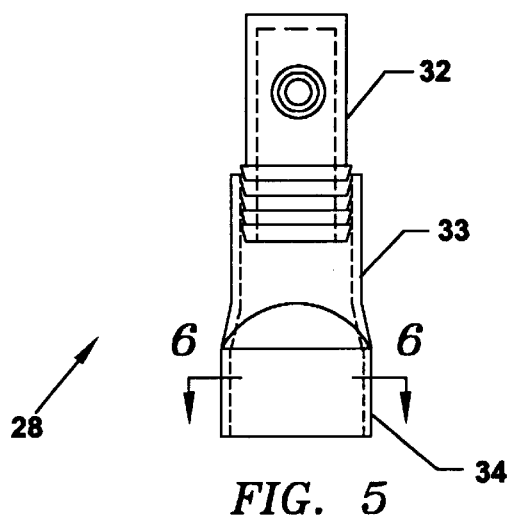
FIG. 5 is a side view of the pressure relief valve.
Figure 4:
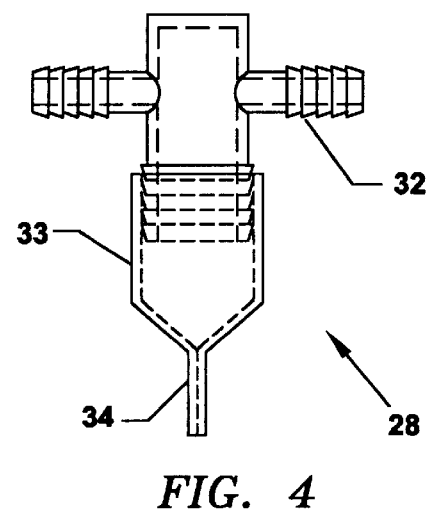
FIG. 4 is a front view of the pressure relief valve.

Referring now to the drawings wherein like numerals designate like and corresponding parts throughout the several views, in FIGS. 1 through 9, inclusive, a uterine balloon apparatus 20, according to the present invention, is shown according to the present invention. In FIG. 1, an inflated balloon 22 is shown inside of a uterus 21. A semi-rigid catheter 24 extends part way into the inflated balloon 22 and facilitates the insertion and removal of the balloon from the uterus 21. At an inner end portion of the catheter 24 there is a series of small apertures 26 for infusing a physiologic fluid 27, such as a normal saline solution, into the balloon 22 after it is inserted into the uterus 21.

The portion of the catheter 24 which is outside of the uterus 21 is connected to a control 23 which is comprised of a pressure relief valve 28, a pressure gauge 29, a combination fill and pressure regulator valve 30 and short lengths of flexible tubing 31. The primary purpose of the control system 23 is to maintain a constant fluid pressure inside of the balloon 22. Another purpose to prevent the pressure inside of the balloon 22 from exceeding a level which could cause premature ejection of the balloon 22 or injure the uterus 21. In a normal operating mode, a desired pressure which is less than a maximum allowable pressure, is maintained constant by gradually discharging some of the physiologic fluid 27 from the balloon 22 when the uterus 21 contracts after childbirth to resume its normal physiologic function.

The pressure relief valve 28 is preferably located close to the uterus 21 assure that the pressure in the balloon 22 will not exceed the maximum limit under all conditions, such as pinched tube 31 or a mal functioning pressure regulator valve 30. Numerous know types of relief valves, such as a ball check valve (not shown) are available for preventing the pressure from exceeding the maximum limit. In FIGS. 3 through 6 a relief valve 28 is shown which is simple in construction with high reliability. The generally cylindrical shaped valve 28 is comprised of a thin resilient wall housing 33 having a pair of flat walls 34 which abut each other to seal the valve 28 when the pressure is below the maximum limit separate and release fluid 27 when the pressure is at the maximum limit. The thickness and durometer of the walls 34 allow the walls 34 to separate and open the valve along the line A—A and discharge fluid 27 when the pressure is at the maximum limit.

Figure 9:
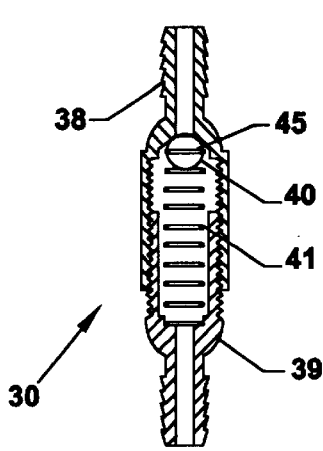
FIG. 9 is a cross-sectional view taken in the same manner as FIG. 8 showing the combination pressure fill and regulator valve in a pressure regulating condition.
Figure 8:
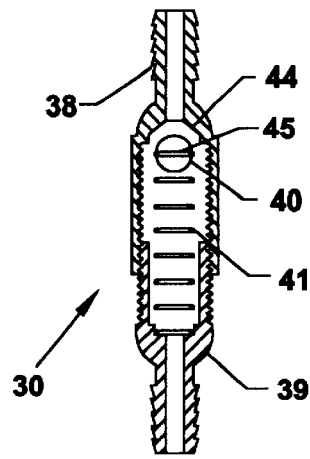
FIG. 8 is a cross-sectional view taken on the line 8—8 in FIG. 7 showing the combination pressure fill and regulator valve in a fill condition.
Figure 7:
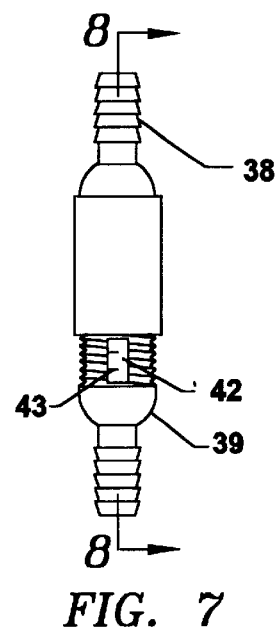
FIG. 7 is an enlarged front view of a combination fill and pressure regulator valve.
Figure 14:
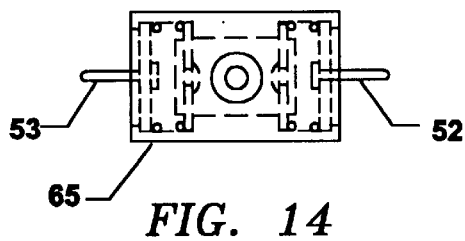
FIG. 14 is a right side view of the high/low pressure switch.
Figure 13:
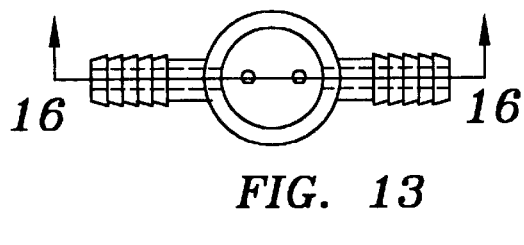
FIG. 13 is an enlarged plan view of a high/low pressure switch.
Figure 16:
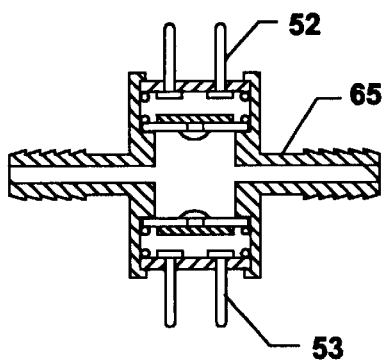
FIG. 16 is a cross-sectional view taken on the line 16—16 in FIG. 13.
Figure 15:
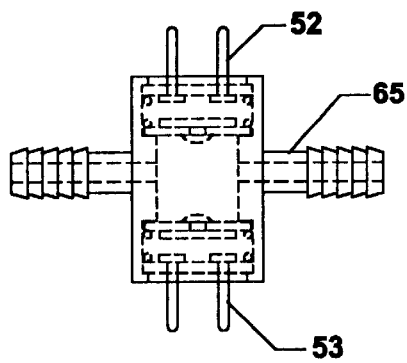
FIG. 15 is front view of the high/low pressure switch.

The pressure gauge 29 preferably consists of an existing type of transducer 36 and an existing type of analog or digital meter 37. The meter 37 is positioned near a patient, to enable a nurse or a physician to monitor the pressure in the balloon when and after liquid is infused but may be or at a remote nurses station for monitoring the pressure. The combination fill and pressure regulator valve 30 is shown in FIGS. 7 through 9. The valve 30 is a ball check valve having an inlet housing 38, an outlet housing 39, a spherical ball 40 and a spring 41. The outlet housing 39 threadably engages the inlet housing 38 with preferably a sealing type thread, such as a dryseal thread. One unique feature of the valve 30 is that an exterior portion 42 of the outlet housing thread is removed and marked with graduations 43 to indicate the relative positions of the inlet 38 and outlet 39 housings. The relative position of the inlet housing 38 and the outlet housing 39 is adjusted by rotating the outlet housing 39 relative to the inlet housing 38.

In FIG. 8, the outlet housing 39 and inlet housing 38 are at a maximum amount of disengagement. The ball 40 is shown withdrawn from a seat 44 of the inlet housing 38 and the valve 30 is open for infusing physiologic fluid 27 through a distal end of the flexible tube 46. When the ball 40 is withdrawn from the seat 44, the ball 40 is retained to the spring 41 by an engagement of an end coil of the spring with a groove 45 of the ball 40. In FIG. 9, the inlet housing 38 has been moved closer to the outlet housing 39 and the ball 40 is engaged with the seat 44 to regulate the pressure in the balloon 22.

The invention is used in the following manner. An empty, deflated balloon 22 is inserted into a bleeding uterus 21 with the assistance of the catheter 24. A warm physiologic solution 27 from an external source (not shown) is infused into the balloon 22 through the distal end of the outlet tube 46. During the infusion of fluid 27, the balloon 22 distends and its effect on bleeding is observed. The pressure gauge 29 may also assist in determining when stop the infusion of the fluid 27 into the uterus 21. The preferred pressure in the balloon 22 is the lowest pressure which counters the bleeding. When this condition occurs, the outlet housing 39 is rotated to set the pressure by cutting off further fluid 27 infusion. The external source of the fluid 27 is disconnected and a drainage bag (not shown) is attached to the outlet tube 46 to capture fluid 27 which is discharged from the balloon 22 to maintain the constant pressure. If the pressure should exceed the maximum allowable pressure, the pressure relief valve 28 opens to prevent the pressure from exceeding the maximum allowable pressure. When periodic contractions of the uterus 21 causes the pressure to rise, the ball 40 is lifted off its seat 44 and fluid 27 is gradually released to maintain the desired pressure. After the uterus 21 has relaxed, and the pressure in the balloon 22 is at the set level, the ball 40 returns to its seat 44 and the pressure regulating valve 30 is closed, preventing a further discharge of fluid 27. Thus, the pressure regulator valve 30 maintains a constant pressure in the balloon 22. If the system should mal-function because of a pinched tube 31 or a faulty regulator valve 30, the pressure relief valve 28 opens to prevent a premature expulsion of the balloon 22 or a rupture of the uterus 21.

In FIGS. 10 through 20 inclusive, a second embodiment 47 is shown comprised of a combination fill and pressure relief valve 48, a low/high pressure warning device 49 and a pressure regulating valve 50. With reference to FIG. 12, the combination fill and pressure relief valve 48 is similar to the pressure relief valve 28 of the first embodiment except for a resilient perforated plug 51 in an upper end portion of the valve 48. The physiologic fluid 27 is infused into the balloon 22 by piercing the valve 48 with a usual hollow needle (not shown) which is attached to the source of the fluid 27. The high/low warning device 49 is shown in FIGS. 13 through 16. It consists of a high/low pressure switch 65, a (normally closed) NC low pressure relay 54, a (normally open) NO high pressure relay 55, and an optical and/or a pair of audio signal generating devices 56 such as a light or buzzer. The high/low pressure switch 65 is a dual switch, i.e. a normally open (NO) low pressure switch 52 and a normally open (NO) high pressure switch 53. The relays 54, 55 and respective signal generating devices are preferably at the same location. Before the balloon 22 is filled with fluid 27, both switches 52, 53 are open. When the balloon 22 is infused with fluid 27, the low pressure switch 52 is closed, causing the low pressure NC low pressure relay 54 to open, and the high pressure switch 53 remains open. When the pressure drops below the minimum limit, the NO low pressure switch 52 opens, causing the NC relay 54 to close and activate the signal generating device 56. When the pressure exceeds a maximum level, the NO high pressure switch 53 closes, causing the NO high pressure relay 55 to close and activate the signal generating device 56. It will be appreciated that a common signal generating device can be used instead of the separate signal generating devices 56.

Figure 19:
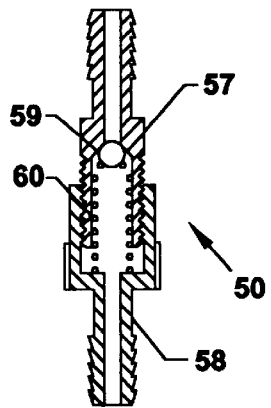
FIG. 19 is a cross-sectional view taken on the line 19—19 in FIG. 18.
Figure 18:
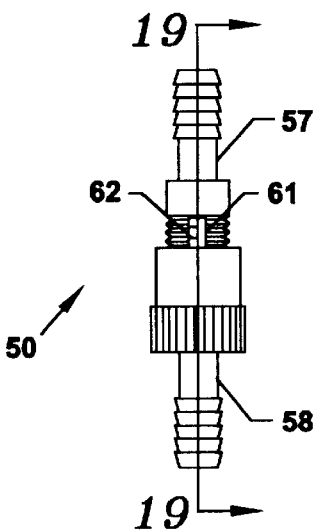
FIG. 18 is a front view of the pressure regulator valve.
Figure 17:
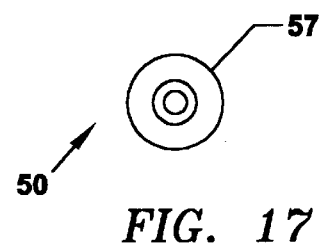
FIG. 17 is an enlarged plan view of a pressure regulator valve.

The pressure regulating valve 50 of the second embodiment 47 is shown in FIGS. 17 through 19, inclusive. The regulating valve 50 is a ball check valve having an inlet housing 57, an outlet housing 58 threadably connected to the inlet housing 57, a ball 59 and a helical spring 60. A threaded portion 61 of the inlet housing 57 has the threads removed and is marked with graduations 62 to set the valve 50 at a desired pressure level.

Figure 20:
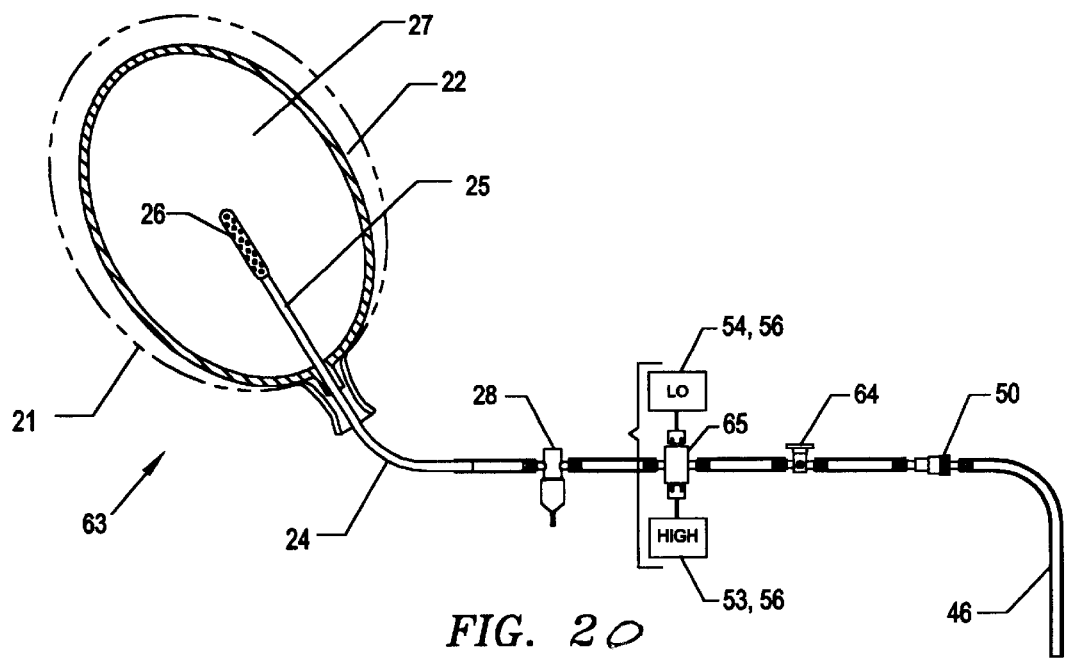
FIG. 20 is a view of a second alternate embodiment of the invention.
Figure 21:
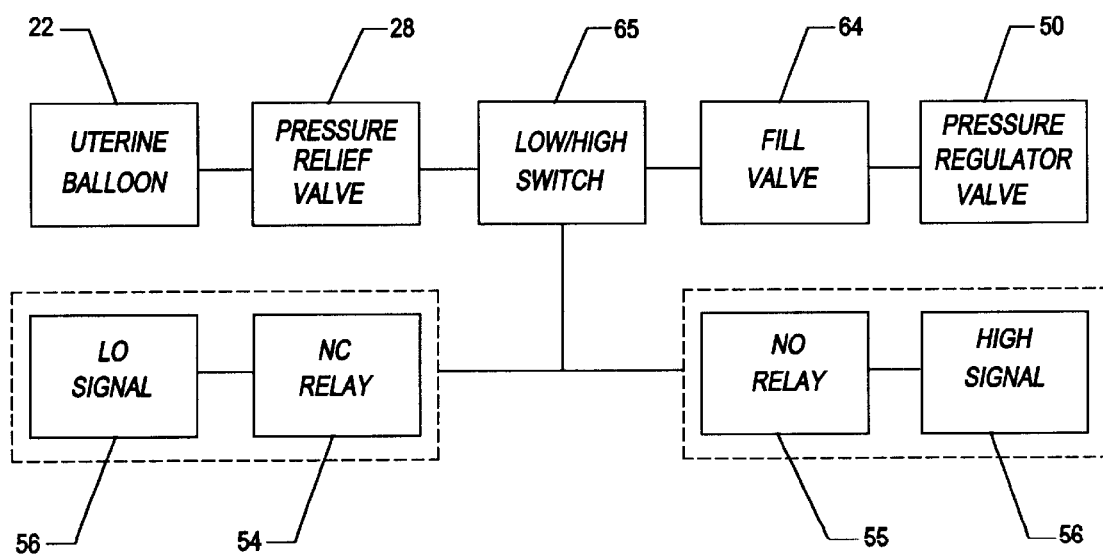
FIG. 21 is block diagram of the second alternate embodiment.

A third embodiment 63 is shown in FIGS. 20 and 21 which is similar to the FIGS. 10 through 20 embodiment, except for the separate pressure relief valve 28 and separate fill valve 64. The pressure relief valve is the same as the valve 28 of the FIGS. 1 through 9 embodiment and the fill valve 64 is a conventional rotary type valve.

From the foregoing it will be understood that my invention provides an effective means for terminating a massive flow of blood in a uterus following childbirth and is an alternative to major surgery, hysterectomies and massive blood transfusions for terminating hemorrhaging in a uterus.

Although only several embodiments have been disclosed for purposes of practicing my invention it will be appreciated that other embodiments can be derived by such changes as substitution of parts, re-arrangements of parts, alternate materials without departing from the spirit thereof.

I claim:

1. A balloon apparatus for terminating maternal hemorrhaging in a distended uterus following childbirth comprised of: an inflatable balloon, said balloon having an inlet portion; a means for inflating said balloon in said uterus by admitting a physiologic fluid into said balloon; a physiological fluid inside of said balloon; and a means for automatically releasing portions of said fluid from said balloon during contractions of said uterus to maintain a constant pressure of said physiologic fluid inside of said balloon.

2. The balloon apparatus recited in claim 1 further comprising a catheter, said catheter having a portion which is connected to said inlet portion of said balloon and extends into an interior of said balloon.

3. The balloon apparatus recited in claim 2 wherein said portion of said catheter which extends into said interior of said balloon has a plurality of apertures for said admitting of said physiologic fluid into said balloon.

4. The balloon apparatus recited in claim 1 further comprising a relief valve located close to said inlet portion of said balloon for automatically discharging fluid from said balloon when said pressure inside of said physiologic fluid inside of said balloon exceeds an established maximum pressure.

5. The balloon apparatus recited in claim 4 wherein said means for automatically preventing said pressure of said physiologic fluid inside of said balloon from exceeding an established maximum pressure and said means for admitting said physiologic fluid into said balloon are comprised of a single valve.

6. The balloon apparatus recited in claim 4 wherein said means for automatically preventing said pressure of said physiologic fluid inside of said balloon from exceeding an established maximum pressure is comprised of a thin wall valve having a pair of thin walls which abut each other to seal the valve when said pressure is below said established maximum pressure and separate when said pressure is above said established maximum pressure to release said fluid.

7. The balloon apparatus recited in claim 1 further comprising a means for determining the level of said pressure of said physiologic fluid inside of said balloon.

8. The balloon apparatus recited in claim 1 further comprising a pressure actuated normally open electrical switch for warning a physician when said pressure of said physiologic fluid inside of said balloon is above an established maximum level.

9. The balloon apparatus recited in claim 8 wherein said means for automatically warning a physician whether said pressure of said physiologic fluid inside of said balloon is above an established maximum level is an audible warning means.

10. The balloon apparatus recited in claim 8 wherein said means for automatically warning a physician whether said pressure of said physiologic fluid inside of said balloon is above an established maximum level is a visual warning means.

11. The balloon apparatus recited in claim 8 wherein said means for automatically warning a physician whether said pressure of said physiologic fluid inside of said balloon is above an established maximum level is comprised of a pressure actuated normally open switch; a normally open relay and a signal generating device.

12. The balloon apparatus recited in claim 1 further comprising a pressure actuated normally closed electrical switch for warning a physician when said pressure of said physiologic fluid inside of said balloon is below an established minimum level.

13. The balloon apparatus recited in claim 12 wherein said means for automatically warning a physician whether said pressure of said physiologic fluid inside of said balloon is below an established minimum level is comprised of a pressure actuated normally open switch; a normally closed relay and a signal generating device.

14. The balloon apparatus recited in claim 1 further comprising a first pressure actuated switch for automatically warning a physician whether said pressure of said physiologic fluid inside of said balloon is above an established maximum level and a second pressure actuated switch for automatically warning said physician when said pressure of said physiologic fluid is below an established minimum level.

15. The balloon apparatus recited in claim 1 further comprising a non visual means for automatically warning a physician whether said pressure of said physiologic fluid inside of said balloon is above or below established pressure levels.

16. The balloon apparatus recited in claim 1 wherein said physiologic fluid is a normal saline solution.

17. The balloon apparatus recited in claim 1 wherein said means for admitting said physiologic fluid into said balloon and said means for automatically discharging portions of said fluid from said balloon to maintain a constant pressure of said physiologic fluid inside of said balloon are comprised of a single valve.

18. The balloon apparatus recited in claim 1 wherein said means for automatically maintaining a constant pressure of said physiologic fluid inside of said balloon is selectively adjustable to change a level of said constant pressure.

19. The balloon apparatus recited in claim 5 wherein said means for determining the level of said pressure of said physiologic fluid inside of said balloon is comprised of a pressure transducer and meter.

20. The balloon apparatus recited in claim 1 wherein said means for automatically releasing portions of said fluid from said balloon to maintain said constant pressure of said physiologic fluid inside of said balloon during said contractions of said uterus is a ball check valve.

21. The balloon apparatus recited in claim 1 wherein said means for admitting said physiologic fluid into said balloon is a perforated resilient plug.

22. A balloon apparatus for terminating maternal hemorrhaging in a distended uterus following childbirth comprised of: an inflatable balloon, said balloon having an inlet portion; a catheter having an end portion operatively connected to said inlet portion of said balloon, said end portion extending into an interior of said balloon; a means for admitting a physiologic fluid into said balloon operatively connected to said balloon; a physiological fluid inside of said balloon; a means operatively connected to said balloon for automatically discharging portions of said physiologic fluid during contractions of said uterus to maintain a constant operating pressure of said physiologic fluid inside of said balloon; and a means for discharging said physiologic fluid from said balloon to prevent said pressure of said physiologic fluid from exceeding an established maximum pressure.

23. A method for preventing loss of an excessive loss of blood from hemorrhaging in a distended uterus following childbirth comprising the steps of:
- inserting an inflatable balloon with the assistance of an operatively connected catheter into said uterus;
- inflating said balloon with a warm physiologic fluid such as a normal saline solution to press said balloon against the walls of said uterus;
- automatically discharging some of said physiologic fluid to maintain a constant operating pressure of said physiologic fluid as said uterus contracts after childbirth to resume its normal physiologic function.

24. The method recited in claim 23 further comprising the step of monitoring the pressure of said physiologic fluid inside of said balloon with a pressure gauge.

25. The method recited in claim 23 further comprising the step of automatically activating an alarm if said pressure of said physiologic fluid inside of said balloon is greater or less than established maximum or minimum pressure levels.

26. The method recited in claim 23 further comprising the step of automatically discharging said physiologic fluid from said balloon when said pressure is greater than an established maximum pressure.

* * * * *